United States Patent [19]

Treuner et al.

[11] 4,053,474
[45] Oct. 11, 1977

[54] PYRAZOLO[4,3-E][1,2,4]TRIAZOLO[4,3-C]PYRIMIDINE

[75] Inventors: Uwe D. Treuner; Hermann Breuer, both of Regensburg, Germany

[73] Assignee: E. R. Squibb & Sons, Inc., Princeton, N.J.

[21] Appl. No.: 678,832

[22] Filed: Apr. 21, 1976

[51] Int. Cl.$^2$ .............. A61K 31/415; C07D 487/14; C07D 401/14; C07D 403/14
[52] U.S. Cl. .............. 260/256.5 R; 260/256.4 F; 424/251; 544/115
[58] Field of Search ............ 260/256.4 F, 256.5 R

[56] References Cited

U.S. PATENT DOCUMENTS 3,787,430  1/1974  Hoehn et al. ............ 260/296 H
3,850,932  11/1974  Kathawala ............ 260/256.4 F

*Primary Examiner*—Donald G. Daus
*Assistant Examiner*—James H. Turnipseed
*Attorney, Agent, or Firm*—Lawrence S. Levinson; Merle J. Smith

[57] ABSTRACT

New pyrazolo[4,3-e][1,2,4]triazolo[4,3-c]pyrimidines have the general formula

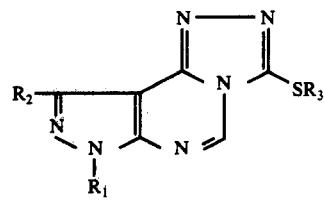

They are useful as antiinflammatory agents.

10 Claims, No Drawings

PYRAZOLO[4,3-e]-[1,2,4]TRIAZOLO-[4,3-c]PYRIMIDINE

SUMMARY OF THE INVENTION

This invention relates to new pyrazolo [4,3-e] [1,2,4]-triazolo [4,3-c] pyrimidines and salt thereof, which have the general formula I.

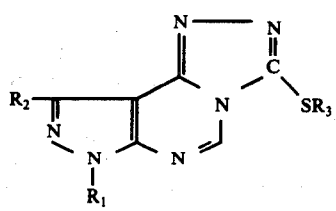

The symbols have the following meanings in formula I and throughout the specification.

$R_1$ and $R_2$ each is hydrogen or lower alkyl;
$R_3$ is hydrogen, a salt forming ion,

lower alkyl or substituted lower alkyl. The lower alkyl substituents are hydroxy, cyano, phenyl,

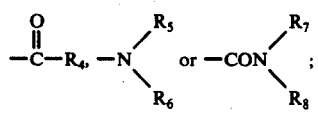

$R_4$ is lower alkyl or phenyl;
$R_5$ and $R_6$ each is hydrogen or lower alkyl or $R_5$ and $R_6$ together with the nitrogen form one of the heterocyclic radicals pyrrolidino, piperidino, morpholino or piperazino;
$R_7$ and $R_8$ each is hydrogen or lower alkyl.

DETAILED DESCRIPTION OF THE INVENTION

In the new compounds having formula I above, the lower alkyl groups represented by the various symbols are straight or branched chain aliphatic hydrocarbon radicals of up to seven carbon atoms, preferably the $C_1$-$C_4$ and especially $C_1$-$C_2$ members. Illustrative are methyl, ethyl, propyl, isopropyl, butyl, isobutyl, t-butyl and the like.

The salt forming ions are metal ions preferably alkali metal or alkaline earth metal ions, e.g., sodium, potassium, calcium, magnesium, etc. The first two are preferred.

Preferred are those compounds of formula I wherein $R_1$ is lower alkyl, especially methyl, and $R_2$ is hydrogen. $R_3$ is preferably hydrogen, lower alkyl or lower alkyl substituted by hydroxy, phenyl or piperidino. When the lower alkyl group is substituted by cyano, lower alkyl,

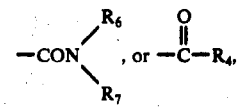

the bridging lower alkyl group preferably has one carbon atom. The examples illustrate particularly preferred embodiments.

The compounds of this invention can be produced by several methods of synthesis.

According to one method a 4-cyano-5-aminopyrazole of the formula

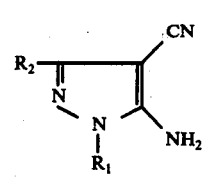

(which is produced, for example, from an unsubstituted or substituted ethoxymethylenemalononitrile and hydrazine or substituted hydrazine) is made to react with an excess of orthoformic acid ester of the formula

III. R—C(OR)$_3$ wherein R is lower alkyl, with heating, to produce an intermediate of the formula

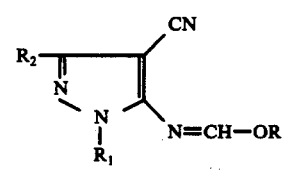

Reaction of the product of formula IV with hydrazine (or its hydrate) at elevated temperature in an organic solvent, e.g., an alcohol like ethanol, yields a product of the formula

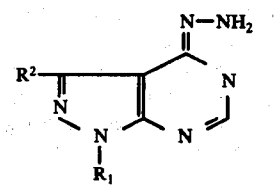

Treatment of this product (V) with an alkali metal alcoholate (met-O-R, wherein met is an alkali metal and R is lower alkyl) in a medium such as dimethylformamide, and then reaction with carbon disulfide results in cyclization and formation of the compound of the formula

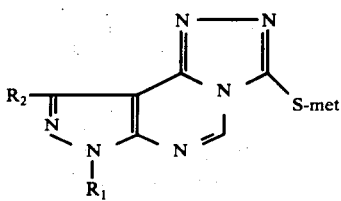
(VI)

Acidification of this product (VI) yields the free mercapto compound, i.e., the compound of formula I wherein $R_3$ is hydrogen. Alkylation of the product of formula VI with an alkylating agent $$XR_3 \qquad (VII)$$

wherein X is a halogen such as iodine, bromine or chlorine and $R_3$ has the meaning defined above other than hydrogen or salt ion, e.g., in a medium such as dimethylformamide at about ambient temperature, provides a product of formula I wherein $R_3$ has any of the meaning defined above except hydrogen or salt ion.

An alternative method of synthesis comprises reacting a pyrazolo [3,4-d]pyrimidine of the formula

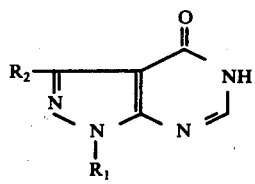
(VIII)

(or its enol form) with a phosphorous oxyhalide like phosphorous oxychloride at elevated temperature to form the halo derivative

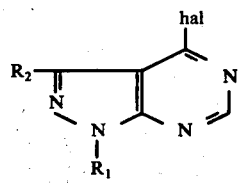
(IX)

wherein hal represents the halogen.

This intermediate of formula IX is then treated with hydrazine or its hydrate in an alcohol like ethanol at about ambient temperature. The same intermediate of formula V above results from this reaction.

The intermediate of formula V can now be treated as described above or it can be made to react with 1,1-thiocarbonyldiimidazole in a medium such as dimethylformamide at a reduced temperature, e.g., about 5°–10° C, to obtain as a product a compound of the formula

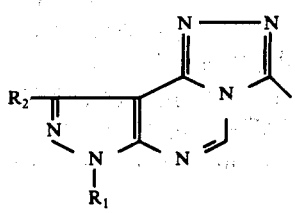
(X)

This product (X) is then optionally alkylated as described above.

The new compounds of this invention have anti-inflammatory properties and are useful as anti-inflammatory agents, for example, to reduce local inflammatory conditions such as those of an edematous nature or resulting from proliferation of connective tissue in various mammalian species such as rats, dogs and the like when given orally in dosages of about 5 to 100 mg/kg/day, preferably 5 to 50 mg/kg/day, in single or 2 to 4 divided doses, as indicated by the carageenan edema assay or delayed hypersensitivity reaction in rats. The active substance is utilized in a composition such as tablet, capsule, solution or suspension containing up to about 500 mg. per unit of dosage of a compound or mixture of compounds of formula I or physiologically acceptable salt thereof. The material is compounded in conventional manner with a physiologically acceptable vehicle or carrier, excipient, binder, preservative, stabilizer, flavor, etc. as called for by accepted pharmaceutical practice. Topical preparations containing about 0.01 to 3 percent by weight of active substance in a conventional lotion, salve or cream can also be used.

The following examples are illustrative of the invention and serve as models for the production of additional members by substitution of the appropriately substituted reactants, all temperatures are in degrees celsius.

EXAMPLE 1 a. 1-Methyl-4-cyano-5-ethoxymethyleneaminopyrazole 222.0 g. of 1-methyl-4-cyano-5-aminopyrazole (produced from ethoxymethylenemalononitrile and methylhydrazine), 279 g. of orthoformic acid triethyl ester (15% excess) and 225 ml. of acetic anhydride are heated at reflux for 3 hours until a clear solution results. The alcohol thus formed, excess orthoester, ethyl acetate and acetic anhydride are distilled off. The oily residue crystallizes on rubbing. The crude product, 1-methyl-4-cyano-5-ethoxymethyleneaminopyrazole, is recrystallized from cyclohexane and obtained in 219 g. yield are colorless crystals, m.p. 48°. The crude product is sufficiently pure for further use.

b. 1,5-Dihydro-1-methyl-4H-pyrazolo[3,4-d]pyrimidin-4-one hydrazone 160 g. of 1-methyl-4-cyano-5-ethoxymethyleneaminopyrazole are dissolved in 1 liter of absolute ethanol and 76.0 g. of hydrazine hydrate are added dropwise with stirring. This mixture is refluxed for 8 hours. After cooling, the product, 1,5-dihydro-1-methyl-4H-pyrazolo-[3,4-d]pyrimidin-4-one hydrazone, is filtered under suction and crystallized from dimethylformamide, yield 135 g., m.p. 231°.

c. 7-Methyl-3-mercapto-7H-pyrazolo[4,3-e][1,2,4]triazolo[4,3-c]-pyrimidine, potassium salt 73 g. of 1,5-dihydro-1-methyl-4H-pyrazolo[3,4-d]pyrimidin-4-one hydrazone are suspended in 350 ml. of dimethylformamide and 49 g. of potassium t-butylate are added. 34.8 g. of carbon disulfide are added dropwise with stirring and, after the addition, the reaction mixture is stirred at 80° for 2 hours and 12 hours at room temperature. After washing with methanol and ether, 55 g. of 7-methyl-3-mercapto-7H-pyrazolo[4,3-e]-[1,2,4]triazolo[4,3-c]pyrimidine, potassium salt are obtained as a light yellow powder, m.p. >300° (CZ). An additional 3.2 g. of the potassium salt are obtained by concentrating the filtrate. By acidifying the potassium salt, the free mercapto compound is obtained as yellowish crystals, m.p. 254°.

EXAMPLE 2

7-Methyl-3-methylthio-7H-pyrazolo[4,3-e][1,2,4]triazolo[4,3-c]pyrimidine

To 3 g. of 7-methyl-3-mercapto-7H-pyrazolo[4,3-e][1,2,4]-triazolo[4,3-c]pyrimidine, potassium salt, in 25 ml. of dimethylformamide, 2.1 g. of methyl iodide are added and the mixture is stirred for 1 hour at room temperature. The reaction mixture is then poured into 200 ml. of water and the product, 7-methyl-3-methylthio-7H-pyrazolo[4,3-e][1,2,4]triazolo [4,3-c]-pyrimidine, is filtered under suction, crystallized from dimethylformamide and obtained as yellowish crystals, m.p. 204°-206°.

The following additional compounds of formula I having the substituent $R_3$ in the table below are obtained by treating 7-methyl-3-mercapto-7H-pyrazolo[4,3-e][1,2,4]triazolo[4,3-d]-pyrimidine, potassium salt, with the halide $XR_3$, wherein X and $R_3$ have the meanings indicated in the table, according to the procedure of Example 2:

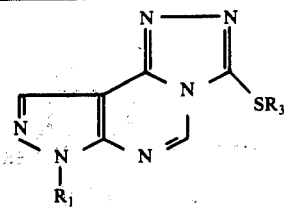

| Ex. | $R_1$ | X | $R_3$ | m.p. °C | Crystallized from |
|---|---|---|---|---|---|
| 3 | $CH_3$ | I | $-C_2H_5$ | 183 | Methyleneglycol |
| 4 | $CH_3$ | Br | $-CH_2-\bigcirc$ | 207 – 208 | Methyleneglycol |
| 5 | $CH_3$ | I | $-C_3H_7$ | 162 | Methyleneglycol |
| 6 | $CH_3$ | Br | $-CH_2-CH\begin{smallmatrix}CH_3\\CH_3\end{smallmatrix}$ | 196 – 197 | Ethanol |
| 7 | $CH_3$ | Br | $-(CH_2)_4-CH_3$ | 148 –150 | Methanol |
| 8 | $CH_3$ | Br | $-CH(CH_3)-(CH_2)_4-CH_3$ | 133 –135 | Ethanol |
| 9 | $CH_3$ | Br | $-(CH_2)_3-\bigcirc$ | 144 – 145 | Ethanol |
| 10 | $CH_3$ | Br | $-(CH_2)_3-OH$ | 153 – 154 | Isopropanol |
| 11 | $CH_3$ | Br | $-CH_2-C(O)-OC_2H_5$ | 142 – 143 | Ethanol |
| 12 | $CH_3$ | Br | $-CH_2-C(O)-\bigcirc$ | 198 | DMF |
| 13 | $CH_3$ | Br | $-CH_2-C(O)-CH_3$ | 196 – 197 | Methyleneglycol |
| 14 | $CH_3$ | Cl | $-(CH_2)_2-N\bigcirc H$ | 169 – 170 | Methyleneglycol |
| 15 | $CH_3$ | Cl | $-(CH_2)_3-N\bigcirc H$ | 135 – 136 | Ethanol |
| 16 | $CH_3$ | Cl | $-CH_2-CN$ | 168 | Methyleneglycol |
| 17 | $CH_3$ | I | $-CH_2-C(O)-NH_2$ | 283 | DMSO |
| 18 | $CH_3$ | Cl | $-C(O)-CH_3$ | 150 | Methyleneglycol |
| 19 | H | Cl | H | | |
| 20 | H | Cl | $-CH_3$ | | |
| 21 | H | Cl | $-(CH_2)_3-OH$ | | |
| 22 | H | Cl | $-CH_2-\bigcirc$ | | |
| 23 | $C_2H_5$ | Br | $-CH_2-C(O)-OC_3H_7$ | | |
| 24 | $C_3H_7$ | Br | $-(CH_2)_2N(CH_3)_2$ | | |
| 25 | $CH_3$ | Br | $-CO-NHCH_3$ | | |

EXAMPLE 26 a. 4-Chloropyrazolo[3,4-d]pyrimidine 31.1 g. of 4-hydroxypyrazolo[3,4-d]pyrimidine are heated at reflux with 200 ml. of phosphorous oxychloride for 12 hours. The excess phosphorous oxychloride is distilled off and the residue is boiled with benzene. After distilling off the benzene and trituration with petroleum ether, there remain 15.8 g. of 4-chloropyrazolo[3,4-d]pyrimidine as light yellow crystals, m.p. 94°-96°. This product is pure enough for further use.

b. 4-Hydrazino-1-methylpyrazolo[3,4-d]pyrimidine 50 g. of 4-chloropyrazolo[3,4-d]pyrimidine are dissolved in 700 ml. of absoulute ethanol and 25 g. of hydrazine hydrate in 100 ml. of ethanol are slowly added dropwise with stirring. This is stirred for 13 hours at room temperature and the product formed is then filtered under suction, water is added and the product, 4-hydrazino-1-methylpyrazolo[3,4-d]pyrimidine, is crystallized from dimethylformamide as yellowish crystals, m.p. 231°.

c. 7-Methyl-3-methylthio-7H-pyrazolo[4,3-e][1,2,4]triazolo[4,3-c]-pyrimidine 3.08 g. of 4-hydrazino-1-methylpyrazolo[3,4-d]pyrimidine and 3.56 g. of 1,1-thiocarbonyldiimidazole in 100 ml. of dimethylformamide are stirred at 5° over a period of 16 hours. The 7-methyl-3-mercapto-7H-pyrazolo[4,3-e][1,2,4]-triazolo[4,3-c]pyrimidine which has been formed is filtered under suction, washed with water and recrystallized from a little dimethylformamide as yellowish crystals, m.p. 252°-254°.

The crystalline free mercapto compound is suspended in dimethylformamide, the calculated amount of potassium methoxide and then 5 g. of methyl iodide are added. After 1 hour, the 7-methyl-3-methylthio-7H-pyrazolo[4,3-e][1,2,4]triazolo[4,3-c]-pyrimidine is filtered under suction, dried and recrystallized from dimethylformamide, yield 2.6 g., m.p. 204°-206°.

The following additional compounds are obtained by the procedures of Example 26.

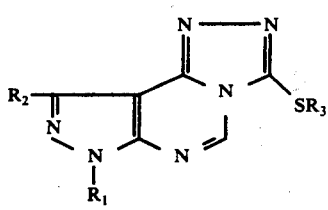

| Example | $R_1$ | $R_2$ | $R_3$ |
|---|---|---|---|
| 27 | $CH_3$ | H | $-CH_2-N\underset{}{\overset{}{\diagdown}}O$ (morpholine) |
| 28 | $CH_3$ | $CH_3$ | $-(CH_2)_2-N\diagdown$ (pyrrolidine) |
| 29 | H | $CH_3$ | $-CH_2-N\diagdown NH$ (piperazine) |
| 30 | $CH_3$ | $CH_3$ | $-CH_2NH_2$ |
| 31 | H | H | $-(CH_2)_2CN$ |
| 32 | $CH_3$ | $C_2H_5$ | $-CH_2OH$ |
| 33 | H | H | $-(CH_2)_2CONHC_2H_5$ |
| 34 | H | $CH_3$ | $-CH_2CON(CH_3)_2$ |
| 35 | $CH_3$ | H | $-CO-C_4H_9$ |

What is claimed is:

1. A compound of the formula

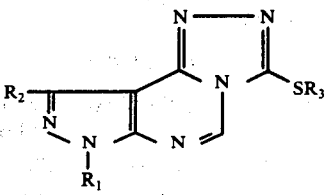

wherein $R_1$ and $R_2$ each is hydrogen or lower alkyl; $R_3$ is hydrogen, alkali metal, alkaline earth metal,

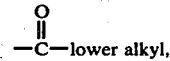

lower alkyl or mono-substituted lower alkyl wherein the lower alkyl substituent is hydroxy, cyano, phenyl,

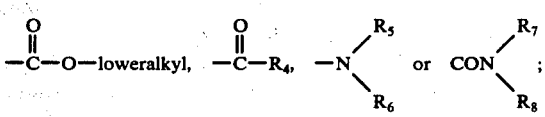

$R_4$ is lower alkyl or phenyl;
$R_5$ and $R_6$ each is hydrogen or lower alkyl; and $R_7$ and $R_8$ each is hydrogen or lower alkyl.

2. A compound as in claim 1 wherein $R_3$ is lower alkyl.

3. A compound as in claim 1 wherein $R_1$ and $R_3$ each is lower alkyl and $R_2$ is hydrogen.

4. A compound as in claim 1 wherein $R_1$ is methyl and $R_2$ is hydrogen.

5. A compound as in claim 4 wherein $R_3$ is lower alkyl.

6. A compound as in claim 4 wherein $R_3$ is ethyl.

7. A compound as in claim 4 wherein $R_3$ is methyl.

8. A compound as in claim 4 wherein $R_3$ is hydrogen.

9. A compound as in claim 4 wherein $R_3$ is hydroxy-lower alkyl.

10. A compound as in claim 4 wherein $R_3$ is hydroxypropyl.

* * * * *